United States Patent
Burgie

Patent Number: 5,126,112
Date of Patent: Jun. 30, 1992

[54] GRAPHITE AND CARBON FELT INSULATING SYSTEM FOR CHLOROSILANE AND HYDROGEN REACTOR

[75] Inventor: Richard A. Burgie, Midland, Mich.

[73] Assignee: Hemlock Semiconductor Corporation, Hemlock, Mich.

[21] Appl. No.: 652,359

[22] Filed: Feb. 7, 1991

Related U.S. Application Data

[63] Continuation of Ser. No. 381,228, Jul. 18, 1989, abandoned.

[51] Int. Cl.⁵ .................... C01B 33/033; B01J 19/02; B32B 9/00
[52] U.S. Cl. .................... 422/241; 428/408; 428/920; 428/282; 428/226; 428/292; 428/138; 428/184; 428/906; 428/213; 428/34.5; 428/37; 428/215; 428/218; 422/129; 422/158; 422/199; 423/349; 423/350
[58] Field of Search ............ 428/408, 920, 282, 226, 428/292, 138, 184, 906, 213, 34.5, 37, 215, 218; 422/129, 158, 241, 199; 423/349, 350

[56] References Cited

U.S. PATENT DOCUMENTS

| | | | |
|---|---|---|---|
| H. 140 | 10/1986 | Bruns et al. | 428/213 |
| 3,343,920 | 9/1967 | Lowe | 422/241 X |
| 3,920,339 | 11/1975 | Fletcher et al. | 428/109 |
| 4,597,948 | 7/1986 | Sanjurjo | 422/241 X |
| 4,617,072 | 10/1986 | Merz | 428/34.4 |
| 4,620,839 | 11/1986 | Moritoki et al. | 428/408 X |
| 4,737,348 | 4/1988 | Levin | 422/241 X |
| 4,888,242 | 12/1989 | Matsuo et al. | 428/408 |
| 4,892,783 | 1/1990 | Brazel | 428/282 |
| 4,971,772 | 11/1990 | Aulich et al. | 422/241 |

OTHER PUBLICATIONS

C. K. Crawford, High-Efficiency High-Temperature Radiation Heat Shields, J Vacuum Science Technology, 9:23 (1972).
E. W. Edstrand, Evolution and Applicability of High Temperature Electric Heating Fiber Modules, Industrial Heating, Nov., 1986.

Primary Examiner—Ellis P. Robinson
Assistant Examiner—William P. Watkins, III.
Attorney, Agent, or Firm—William F. Boley

[57] ABSTRACT

The present invention relates to an insulation system for a high temperature reactor in which chlorosilanes and hydrogen gases are present. The system described comprises an inner graphite radiant heat shield and an outer carbon-based, rigid, felt insulation of high density. The inner radient heat shield provides increased chemical stability at the hot face in a chlorosilane and hydrogen reactor. Also, the inner radient heat shield reduces the temperature at the interface with the carbon-based rigid felt, thereby reducing the reactivity of the chlorosilanes with the carbon-based rigid felt. The high density of the carbon-based rigid belt further reduces radiant heat loss. More importantly, the high density of the carbon-based rigid felt excludes the highly heat conductive hydrogen gas from the voids of the flet. The insulation system, as described, allows reactors containing chlorosilanes and hydrogen gases to be operated at higher and more efficient temperatures for longer periods of time.

15 Claims, 1 Drawing Sheet

GRAPHITE AND CARBON FELT INSULATING SYSTEM FOR CHLOROSILANE AND HYDROGEN REACTOR

This is a continuation of copending application Ser. No. 07/381,228 filed on Jul. 18, 1989, now abandoned.

BACKGROUND OF THE INVENTION

The present invention relates to an improved insulation system for a reactor used to react chlorosilanes and hydrogen gases. The system described comprises an inner graphite radiant heat shield and an outer carbon-based rigid felt insulation of high density.

The reaction of hydrogen with chlorosilanes requires a temperature in the range of 500° C. to 1100° C. The kinetics of these reactions are improved at higher temperatures. However, the ability to achieve and maintain higher temperatures within the reactor is limited by the economics required to provide the additional radiant heat and the ability of the reactor to tolerate the additional heat. The preferred method to maintain higher temperatures within the chlorosilane and hydrogen reactor is by improved insulation. However, increased insulation alone is not enough; the insulation must be capable of withstanding the higher temperatures created.

Insulations fabricated from carbon and graphite are known to have high heat stability. However, these carbon based insulation materials, when used in a chlorosilane and hydrogen reactor, have been found to react with hydrogen to form methane and with chlorosilanes to form silicon carbide. These reactions reduce the insulating capacity of carbon based insulation as well as reduce the structural integrity.

The three generally accepted modes of heat transfer through insulation are by electromagnetic radiation, conduction, and convection. Electromagnetic radiation heat transfer predominates at temperature above about 1000° C., but at temperatures below about 1000° C. conduction and convection become increasingly important as the mode of heat transfer. In general, density and reflective properties make a material effective against electromagnetic radiation heat loss. However, as the density of a material increases the heat loss due to conduction increases. Therefore, to reduce heat loss as a result of conduction through the materials, insulations are typically made of low density felts.

Current art suggests that an improved high temperature insulation can be achieved by combining a series of radiation shields with a low density, flexible, felt insulation. The number of radiation shields required to drop the temperature to a point below which radiation predominates as the principal form of energy loss can be estimated by standard means. C. K. Crawford, J. Vac. Sci. Technol. 9:23, 1972. The art teaches a low density felt can be used in areas of a furnace where conductive and convective energy becomes of increasing importance.

It is known that the thermal conductivity of hydrogen is greater than that of air. Edstrand, E. W., *Evolution and Applicability of High Temperature Electric Heating Fiber Modules*, Industrial Heating, November, 1986, teaches that, in insulation made from ceramic fiber, the presence of hydrogen gas can increase heat loss dramatically. Edstrand suggests improved insulating capabilities can be realized when the ceramic fiber insulation has a density of 12 lb/ft$^3$ or more. Edstrand does not provide any information on the effect of the presence of hydrogen gas on insulation made from carbon based materials.

The present invention provides a thermal insulating system for a chlorosilane and hydrogen reactor. It was recognized during the development of this invention that minor amounts of chlorosilanes and hydrogen gases may escape from the reactor and come in contact with the insulation. The insulating system design of the present invention reduces the impact of the reactions of the escaped chlorosilanes and hydrogen gases with carbon-based felt insulation. Also, the thermal insulating system design recognizes the impact of hydrogen gas on heat transfer through a carbon-based felt and reduces this impact. The thermal insulation system design allows the chlorosilane and hydrogen reactor to be operated at higher and more efficient temperatures for longer periods of time.

BRIEF DESCRIPTION OF THE INVENTION

The present invention is a high temperature insulating system for use around a reactor containing chlorosilane and hydrogen gases. The thermal insulating system consists of an inner radiation shield of graphite and an outer rigid felt insulating material. The invention, as described, reduces loss of insulation ability of the carbon-based felt insulation. This improvement is achieved by using a graphite radiant heat shield to reduce the interfacial temperature between the graphite radiant heat shield and dense carbon-based felt to below about 1000° C., at which temperature the carbon-based felt is less reactive with hydrogen and chlorosilanes. The carbon-based outer rigid felt insulating layer is of a density which compensates for the increased thermal conductivity of hydrogen gas. This design of the thermal insulating system allows chlorosilane and hydrogen reactors to be operated at higher and more efficient temperatures for longer period of times, than those which can be achieved with current insulating methods used for chlorosilane and hydrogen reactors.

BRIEF DESCRIPTION OF THE DRAWINGS

For a better understanding of the invention, reference may be made to the embodiments exemplary of the invention shown in the accompanying drawings wherein.

DETAILED DESCRIPTION OF THE DRAWINGS

Figure 1:
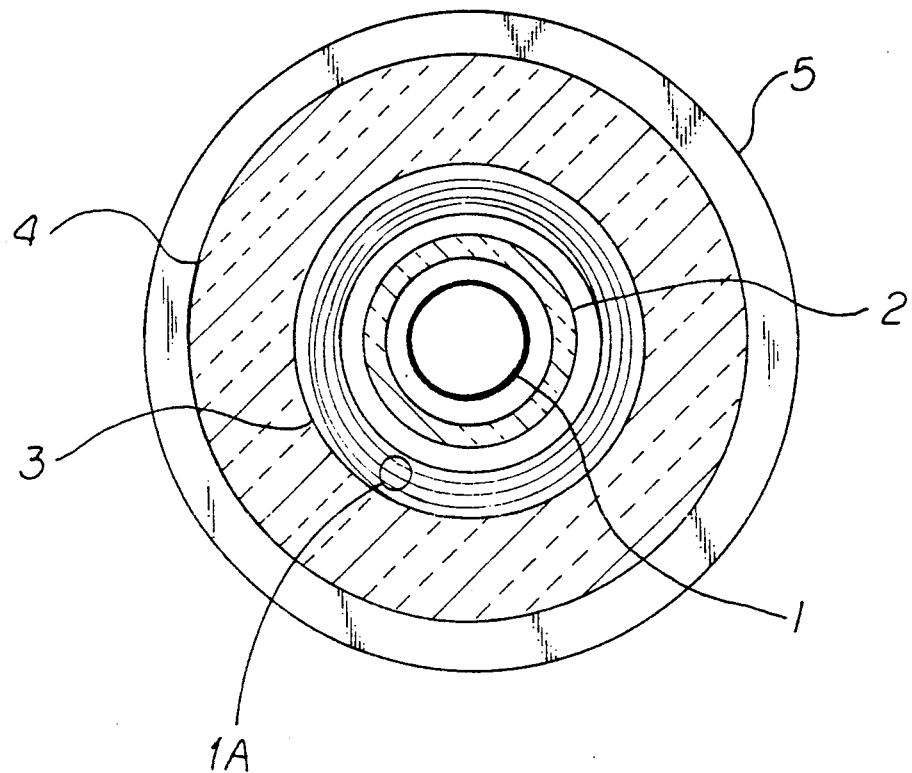
FIG. 1 is a cross-sectional view of a reactor employing the insulation system of the instant invention.

As illustrated in FIG. 1, one embodiment of the instant invention comprises an enclosed reaction area 1 with adjacent heating elements 2. Surrounding the heating elements 2, is a thermal insulating system consisting of an inner radiant heat shield 3 and an outer carbon-based rigid felt insulation layer 4. The insulated reactor is enclosed in a pressure vessel shell 5.

Figure 1A:
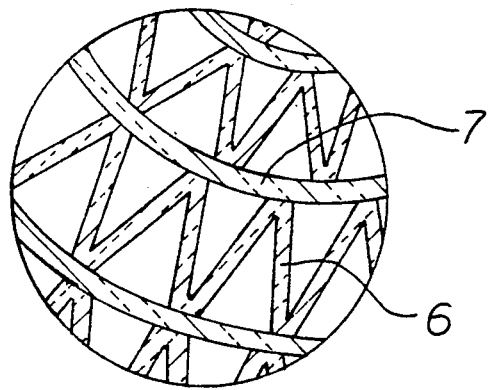
FIG. 1A is an expanded cross-sectional view of an embodiment of the radiant heat shield, which comprises a portion of the instant claimed insulation system.

FIG. 1A is an expanded cross-sectional view of the inner radiant heat shield 3. The expanded view shows an individual wrap 7 of the inner radiant heat shield 3 separated by a spacing means 6 consisting of a corrugated sheet.

DESCRIPTION OF THE INVENTION

The present invention is a thermal insulating system for a high temperature reactor containing chlorosilane and hydrogen gases. The thermal insulating system comprises: (A) an inner radiant heat shield formed from graphite; and (B) an outer carbon-based rigid felt insulation layer.

The term thermal insulating system denotes that the described invention is a combination of elements into a system which extends the insulating abilities of carbon-based insulation materials when used around a reactor containing chlorosilane and hydrogen gases; some of said gases leaking outside the reactor and contacting the insulating system. The thermal insulation system consists of an inner layer which is most effective against electromagnetic radiant heat loss and an outer layer which is more effective against convective and conductive heat losses. In the carbon-based system described, it is believed that at temperatures above about 1000° C. electromagnetic radiation is the principle method of heat conduction. Below 1000° C. conductive and convective heat losses become more important. Therefore, in order for the thermal insulating system of the present invention to be effective, a high temperature reactor is one where the inner hot face temperature of the insulation will be greater than about 1000° C. Also, at temperatures above about 1000° C., carbon-based felt reacts significantly with hydrogen gas to form methane and with chlorosilane gas to form silicon carbide. The temperature reduction offered by the radiant heat shield reduces the temperatures experienced by the carbon-based felt to minimize these destructive reactions and protect the insulating ability and structural integrity of the carbon-based felt insulation.

The chlorosilane to be reacted can be any material containing a chlorine bound to silicon. The chlorosilane can be mono-, di-, tri- or tetrachlorosilanes or mixtures thereof. The chlorosilane can be disilanes containing chloride. The chlorosilane can be, for example, trimethylchlorosilane, tetrachlorosilane, hexachlorodisilane, or heptamethylchlorodisilane.

The inner radiant heat shield is formed from graphite. Preferred is anisotropic graphite. By anisotropic graphite is meant, graphite with the plane of the crystals arranged such that higher resistance to heat conduction exists perpendicular to the plane of the crystals than within the plane. This type of arrangement minimizes heat conduction through the shield while allowing for a more even heat distribution within the shield. The more even heat distribution within the shield helps reduce localized hot spots and buckling of the shield. It is also believed the anisotropic nature of the graphite provides increased chemical stability to the material. The density of the graphite inner radiant heat shield can be about 20 lb/ft$^3$ to about 110 lb/ft$^3$. Preferred is a density of about 70 lb/ft$^3$. The density of the material contributes to the chemical stability as well as the structural integrity of the shield.

The radiant heat shield is constructed from a continuous sheet of the graphite material wound in a spiral for a requisite number of wraps. The number of wraps refers only to the number of windings of the continuous graphite sheet around the reactor. The spacing means, for example, a corrugated sheet of anisotropic graphite is not considered as a separate wrap, when present. The thickness of the graphite shield material is determined by requirements for electromagnetic radiation translucence, flexibility, and size restrictions. In general, a lower limit of 1 micron in thickness of the graphite material will provide the requisite electromagnetic radiation translucent requirements. However, in practice a thickness of 0.005 to 0.030 inches has been shown to be practical for structural integrity and fabrication of the shield. Although thicker material can be used, the thickness limits the number of wraps which can be designed into an effective shield. A preferred material of construction for the radiant heat shield is a continuous anisotropic graphite sheet about 0.015 inches in thickness.

The number of wraps of the graphite radiant heat shield are determined such as to reduce the temperature at the interface of the radiant heat shield with the carbon-based rigid felt to below about 1000° C. Standard methods exist for estimating the number of such wraps. Crawford, C. K., J. Vac. Sci. Technol. 9:23 (1972). In practice, these calculations only provide a rough approximation of the required number of wraps and the actual number must be determined by experimentation. The number of wraps depend in part on the required temperature drop which is in turn dependent upon the hot face temperature. The number of wraps also depend upon overall heat transfer by conduction and radiation within the radiant heat shield. Heat convection within the radiation shield is considered to be negligible.

The required number of wraps of the sheet of graphite material comprising the radiant heat shield depends in part upon the emissivity of the graphite material. An emissivity in the range of about 0.4 to 0.6 at 1500° C. is considered to be useful for the present invention. Preferred is a material with an emissivity of about 0.5.

The required number of wraps of the sheet of graphite material comprising the radiant heat shield is also dependent upon heat conduction at contact points between the wraps. The contact points serve as a source of heat conduction through the shield, thus, reducing the insulating capacity of the shield. Therefore, the wraps must be spaced such as to minimize such contact. Conductive heat loss of a radiation heat shield is also a function of the ratio between the hot face of the shield and the cool face. The closer this ratio is to one, the more effective the radiation heat shield. Therefore, when constructing the heat shield the spacing is critical to minimize contact while preventing the shield from becoming too thick such that the inner and outer shield ratio is considerably greater than one. Considering all of these factors, a workable number of wraps is considered to be in the range of 5 to 85. A preferred number of wraps, when the hot face temperature is about 1300° C. to 1550° C. and the spacing center to center of the wraps is 0.01 to 0.09 inches, is 20 to 30. Most preferred under these conditions is 28 wraps. When the spacing center to center of the wraps is about 0.01 inch, the preferred number of wraps is 60 to 75. Under the condition described, a typical useful thickness for the radiant heat shield is about ⅜ inch to about 2½ inches.

In a preferred embodiment of the present invention the wraps of the radiant heat shield are separated by spacers. The spacers can be formed from carbon or graphite. The spacers can be, for example, in the form of individual strands or spots, a mesh, or a perforated sheet. In a preferred embodiment of the present invention, the spacer is a corrugated anisotropic graphite sheet attached to one side of the graphite sheet comprising the radiant heat shield. The spacer material can be attached to the graphite sheet comprising the radiant heat shield by known means, for example, a carbon based adhesive. It is important that the thickness of the spacer be adequate to prevent contact of the individual wraps of the radiant heat shield with each other, without contributing unnecessarily to the overall thickness of the shield. Preferred are spacers of a thickness of about 0.001 inch to about 0.020 inch, but the thickness may be as great as about 0.030 inch. A combination of spacing means can be used within a radiant heat shield. For example, the inner wraps of a radiant heat shield can be separated by a fibrous spacing means while the outer wraps can be separated by a corrugated sheet spacing means. Radiant heat shields are known materials and are available commercially, for example, fabricated GRAFOIL ® heatshields manufactured by Union Carbide Corporation, UCAR Division, Cleveland, Ohio.

A layer of a carbon-based rigid felt is placed around the exterior of the radiant heat shield. Below about 1000° C. conductive and convective heat losses normally become more important than radiant heat losses, therefore, a felt is a more effective insulation. The felt can be formed from either carbon or graphite.

It has been discovered that the use of rigid, high density, carbon-based felt is critical to a successful insulation system for a chlorosilane and hydrogen reactor. The use of a high density carbon-based felt is contra to what is taught in prior art for carbon-based insulations.

In considering the appropriate density of felt, a trade-off must be made between the conduction of heat through the fibers and the conduction of heat by the gas occupying the voids of the felt. In air or nitrogen environments, heat loss through carbon-based felt occurs primarily by conduction through the fibers at temperatures below about 1000° C. Therefore, lower density materials of about 5 lb/ft$^3$ are often preferred. However, the hydrogen gas employed in the reactor of the present invention has a thermal conductivity approximately seven times greater than that of air or nitrogen. Therefore, heat conduction through the felt voids containing hydrogen plays a proportionally greater role in heat loss. Because of the higher heat conduction of hydrogen, it has been found that higher density carbon-based felt materials with reduced voids provide a superior insulation for the chlorosilane and hydrogen reactor. The higher density of the materials also reduces radiation heat transfer, which helps to offset any increase in fiber conduction.

The density of the carbon-based felt is not only important to the insulating capability of the felt, but is also important to the structural integrity of the insulation. The increased density contributes to the rigidity of the material. It is critical to the instant invention that the carbon felt be rigid to prevent material collapse in the event of minor methanization and silicon carbide formation at the interface with the radiant heat shield.

Materials such as carbon fiber or graphite fiber felts with densities from about 10 lb/ft$^3$ to 50 lb/ft$^3$ are considered beneficial. Preferred are materials with a density from about 20 lb/ft$^3$ to about 30 lb/ft$^3$. Most preferred is a material with a density of about 25 lb/ft$^3$. Carbon-based felts, within the range of densities specified, can be obtained commercially from Union Carbide Corporation, UCAR Division, Cleveland, Ohio.

The thickness of the carbon-based felt used will depend both upon the space available within the reactor and the temperature drop required. A thickness of about ½ inch to 12 inches is considered to be beneficial. Preferred is a carbon-based felt with a thickness of about 1 inch to about 6 inches.

The following examples are presented to be illustrative of the instant invention and are not to be construed as limiting the instant invention as delineated in the claims.

EXAMPLE 1

(Not Within the Scope of the Present Invention)

A study was conducted to determine the causes for failure of carbon felt insulation when used as insulation around a reactor containing chlorosilanes and hydrogen. The feed materials were heated to above the reaction temperature by a 1400° C. to 1550° C. graphite resistive heating system located in the reactor and surrounded by the insulating material. The insulating material consisted of a 6 inch thick layer of carbon felt with a density of 10.5 lb/ft$^3$. The process was run for a total of 190 days at which time the outer shell temperature of the reactor pressure vessel had risen to a point that required shutting down the reactor.

The insulating carbon felt of the reactor was removed and examined both visually and by means of standard analytical techniques for type and cause of failure. A cross-section of the removed insulation was prepared and examined visually for changes. Proceeding from the inner diameter of the insulation to the outer diameter, three regions could be identified. An inner region, region A, consisted of 6-9% of the total thickness of the insulation, was of high density and possessed good structural integrity. A middle region, region B, consisted of 25-50% of the total thickness of the insulation, was of low density and had poor structural integrity. And, an outer region, region C, which consisted of 38-62% of the total thickness of the insulation. Region C consisted of unreacted carbon felt.

In addition, samples where prepared from each of the three regions for gravimetric and chemical analysis. Approximately 1 gram samples from each area were pulverized and weighed into platinum crucibles. Free carbon was determined from the loss in sample weight after firing in air at 950° C. for at least 4 hours.

Samples were further treated with a hydrofluoric-nitric acid mixture (50:50 volume/volume) followed by drying of the sample by heating. The samples were then refired in air at 950° C. for 16 hours. This procedure removed free silicon as gaseous SiF$_4$. The final remaining weight was considered to be silicon carbide. The reduction in weight caused by this process was reported as free silicon. The result of this analysis is presented in Table 1.

TABLE 1

| Region[1] | Sample No. | Carbon (Wt %) | Silicon (Wt %) | Silicon Carbide (Wt %) |
|---|---|---|---|---|
| A | 1 | 7.93 | 5.43 | 86.64 |
| A | 2 | 0.00 | 7.84 | 92.16 |
| A | 3 | 2.74 | 1.80 | 95.45 |
| A-B | 1 | 0.00 | 7.73 | 92.77 |
| A-B | 2 | 3.22 | 9.06 | 87.72 |
| B | 1 | 0.50 | 6.63 | 92.87 |
| B | 2 | 0.00 | 0.82 | 99.28 |
| C | 1 | ~100.00 | 0.00 | 0.00 |
| C | 2 | ~100.00 | 0.00 | 0.00 |
| C | 3 | ~100.00 | 0.00 | 0.00 |

TABLE 1-continued

| Region[1] | Sample No. | Carbon (Wt %) | Silicon (Wt %) | Silicon Carbide (Wt %) |
|---|---|---|---|---|
| C | 4 | ~100.00 | 0.00 | 0.00 |

[1]Region A: Inner 0.5–1.0 inch.
Region B: 1.0–4.0 inches.
Region C: Outer layer The data presented in Table 1 indicate that much of the inner 4 inches of standard carbon felt insulation, density 10.5 lb/ft$^3$, is converted to silicon carbide. Silicon carbide is a good thermal conductor, providing continuing heat at the interface of the silicon carbide with the carbon-based insulation. Therefore, the silicon carbide layer can gradually grow outward until the carbon-based insulation fails.

EXAMPLE 2

The stability of various insulating materials in a hydrogen and chlorosilane environment were tested. Samples of the test materials were placed in the reactor as described in Example 1. At the end of the operating cycle the reactor was cooled and the test samples were evaluated for weight loss. The results of this evaluation are presented in Table 2.

TABLE 2

| Material | Time (hrs) | Weight (g) Before | Weight (g) After |
|---|---|---|---|
| Silica | 2033 | 245 | 0.0 |
| Alumina | 140 | 10 | 0.0 |
| Mullite (3Al$_2$O$_3$.2SiO$_2$) | 140 | 13 | 0.0 |
| Carbon Felt (25 lb/ft$^3$) | 8 | 7.6 | 7.6 |
| Carbon Felt (11.7 lb/ft$^3$) | 8 | 2.1 | 2.0 |
| Carbon Felt (10.5 lb/ft$^3$) | 8 | 3.8 | 3.8 |
| Carbon Felt (5.0 lb/ft$^3$) | 8 | 2.0 | 2.0 |

The data in Table 2 suggest that carbon and graphite based materials have better stability in the test environment than standard insulation materials such as silica, alumina, and mullite.

EXAMPLE 3

The outer shell temperature over time of a chlorosilane and hydrogen reactor insulated with the thermal insulating system of the instant invention was determined. This shell temperature was compared with the shell temperature of a similar reactor insulated with low density carbon felt.

A process employing chlorosilane and hydrogen gases was ran in the reactor. The feed materials were heated above the reaction temperature by a 1400° C. to 1550° C. graphite resistive heating system located in the reactor and surrounded by the insulating material.

The thermal insulating system representing an embodiment of the instant invention consisted of an inner radiant heat shield and an outer rigid felt layer. The inner radiant heat shield was formed from a continuous sheet of anisotropic graphite foil, to one side of which had been attached a corrugated sheet of anisotropic graphite foil to act as a spacer. The anisotropic graphite foil had a thickness of about 0.015 inches and density of about 70 lb/ft$^3$. The combined thickness of the sheet corrugated-sheet composition was about 0.09 inches in thickness. The graphite sheet and corrugated sheet composite was coiled in a spiral 2½ inches thick, comprising 28 wraps. The radiant heat shield, as described, was then surrounded with 6 inches of rigid graphite felt having a density of 25 lb/ft$^3$ (UCAR graphite felt, Union Carbide Corporation, UCAR Division, Cleveland, Ohio). The reaction was ran twice in this reactor.

A similar process was ran in two similar reactors using a six inch layer of carbon felt with a density of 10.5 lb/ft$^3$ as insulation without the radiant heat shield.

As an indication of change in insulating abilities of the insulations, the external temperatures of the shell of the reactors were monitored daily over at least a 4 month period. The results of these measurements are presented in Table 3.

TABLE 3

| Run | Insulation | Average Temp. Change °C./Month |
|---|---|---|
| A | Carbon Felt (10.5 lb/ft$^3$) | 4.0 |
| B | Carbon Felt (10.5 lb/ft$^3$) | 0.8 |
| C | Shield + Graphite Felt (25 lb/ft$^3$) | −1.3 |
| D | Shield + Graphite Felt (25 lb/ft$^3$) | −4.7 |

The data presented in Table 3 indicates that wherein the insulating ability of standard carbon felt decreases with time, no comparable decrease is seen with the radiant heat shield/rigid felt combination of the instant invention.

What is claimed is:

1. A high temperature reactor containing chlorosilane and hydrogen gases comprising:
   A reaction chamber for contacting said chlorosilane and hydrogen gases at temperatures greater than about 1000° C.; the outside of said reaction chamber insulated by a thermal insulating system comprising (A) an inner radiant heat shield formed from continuous spiral wrapped sheet of anisotropic graphite separated by a spacing means between wraps and (B) an outer carbon-based rigid felt insulation layer, the carbon-based rigid felt having a density within a range of 20 to 30 lb/ft$^3$.

2. The high temperature reactor of claim 1, where the spacing means is a corrugated sheet.

3. The high temperature reactor of claim 2, where the corrugated sheet is fabricated from anisotropic graphite.

4. The high temperature reactor of claim 2, where the corrugated sheet is fabricated from carbon.

5. The high temperature reactor of claim 1, where the spacing means is a perforated sheet.

6. The high temperature reactor of claim 1, where the spacing means is in the form of fibers.

7. The high temperature reactor of claim 1, where the inner radiation heat shield is a continuous spiral wrapped sheet of 5 to 85 wraps.

8. The high temperature reactor of claim 7 where the inner radiation heat shield is a continuous spiral wrapped sheet of 20 to 30 wraps.

9. The high temperature reactor of claim 1, where the sheet of anisotropic graphite and the spacing means have a combined thickness of about 0.01 to 0.09 inch.

10. The high temperature reactor of claim 9, where the inner radiation heat shield is about 2½ inches thick, the spacing means is a corrugated sheet of anisotropic graphite, combined thickness of the spacing means and the sheet of anisotropic graphite is about 0.09 inches, and the number of wraps is 28.

11. The high temperature reactor of claim 1, where the outer carbon-based rigid felt insulation layer is composed of carbon fiber.

12. The high temperature reactor of claim 1, where the outer carbon-based rigid felt insulation layer is composed of graphite fiber.

13. The high temperature reactor of claim 1, where the inner radiation heat shield is about $2\frac{1}{2}$ inches thick, the spacing means is a corrugated sheet of anisotropic graphite, combined thickness of the spacing means and the sheet of anisotropic graphite is about 0.09 inches, the number of wraps is 20 to 30, and the outer carbon-based rigid felt insulation layer is composed of graphite fiber.

14. The thermal insulating system of claim 1, where the inner radiation heat shield is about $\frac{5}{8}$ inch thick, the spacing means is a fiber formed from anisotropic graphite, the combined thickness of the spacing means and the sheet of anisotropic graphite is about 0.01 inch, and the number of wraps is 60 to 75.

15. The thermal insulating system of claim 1, where inner wraps of the radiant heat shield are separated by the spacing means in the form of fibers and outer wraps of the radiant heat shield are separated by the spacing means in the form of a corrugated sheet.

* * * * *